(12) United States Patent
Watts

(10) Patent No.: US 12,083,362 B2
(45) Date of Patent: Sep. 10, 2024

(54) TO LINEAR ACCELERATORS

(71) Applicant: WIP INNOVATIONS PTY LTD, Bushland (AU)

(72) Inventor: Jonathan Michael Watts, Bushland Beach (AU)

( * ) Notice: Subject to any disclaimer, the term of this patent is extended or adjusted under 35 U.S.C. 154(b) by 574 days.

(21) Appl. No.: 17/058,200

(22) PCT Filed: May 24, 2019

(86) PCT No.: PCT/AU2019/050519
§ 371 (c)(1),
(2) Date: Nov. 24, 2020

(87) PCT Pub. No.: WO2019/222814
PCT Pub. Date: Nov. 28, 2019

(65) Prior Publication Data
US 2021/0162241 A1    Jun. 3, 2021

(30) Foreign Application Priority Data
May 25, 2018 (AU) .................... 2018901829

(51) Int. Cl.
*A61N 5/10*    (2006.01)
*H05H 7/00*    (2006.01)
(Continued)

(52) U.S. Cl.
CPC ......... *A61N 5/1081* (2013.01); *A61N 5/1075* (2013.01); *H05H 7/22* (2013.01);
(Continued)

(58) Field of Classification Search
None
See application file for complete search history.

(56) References Cited

U.S. PATENT DOCUMENTS 5,947,981 A * 9/1999 Cosman ................. A61B 90/16
128/869
7,188,999 B2 * 3/2007 Mihara ................ A61N 5/1082
378/197
(Continued)

FOREIGN PATENT DOCUMENTS

| CN | 1870940 A | 11/2006 |
|---|---|---|
| CN | 101810910 A | 8/2010 |

(Continued)

OTHER PUBLICATIONS

International Search Report in corresponding PCT application No. PCT/AU2019/050519, Jul. 26, 2019, 5 pp.
(Continued)

*Primary Examiner* — Srinivas Sathiraju
(74) *Attorney, Agent, or Firm* — Tredecim LLC; Sean L. Sweeney

(57) ABSTRACT

The invention relates to a drum assembly for a linear accelerator, the drum assembly comprising a drum having a front face including a front rim and a rear face including a rear rim, one or more support wheels supporting the drum, an arm extending from the front face of the drum and including a beam collimator through which a beam of radiation is emitted to form a radiation isocentre. One or more rear rim members are associated with the rear rim, the rear rim members adapted to substantially offset isocentre distortion due to unintended movement of the drum assembly. The invention also relates to variants thereto and combinations thereof.

20 Claims, 10 Drawing Sheets

(51) Int. Cl.
*H05H 7/22* (2006.01)
*H05H 9/04* (2006.01)
(52) U.S. Cl.
CPC ......... *H05H 9/04* (2013.01); *H05H 2007/007* (2013.01); *H05H 2277/11* (2013.01)

(56) References Cited

U.S. PATENT DOCUMENTS

| | | | | |
|---|---|---|---|---|
| 7,349,523 | B2* | 3/2008 | Jenkins | A61N 5/1048 378/65 |
| 7,616,735 | B2* | 11/2009 | Maciunas | A61N 5/103 378/65 |
| 8,239,005 | B2* | 8/2012 | Wright | A61N 5/1049 600/427 |
| 2004/0184579 | A1* | 9/2004 | Mihara | A61N 5/1049 378/65 |
| 2005/0080332 | A1* | 4/2005 | Shiu | A61B 6/032 600/417 |
| 2006/0079764 | A1* | 4/2006 | Wright | A61B 90/36 600/431 |
| 2007/0023699 | A1 | 2/2007 | Yamashita et al. | |
| 2010/0317968 | A1* | 12/2010 | Wright | A61B 90/36 250/492.3 |
| 2015/0126801 | A1 | 5/2015 | Matteo et al. | |
| 2017/0036042 | A1 | 2/2017 | Bergfjord et al. | |
| 2017/0189720 | A1 | 7/2017 | Liu et al. | |
| 2019/0054322 | A1* | 2/2019 | Yang | A61N 5/1081 |
| 2019/0175951 | A1* | 6/2019 | Yu | A61B 6/032 |
| 2020/0030637 | A1* | 1/2020 | Yang | A61N 5/1081 |
| 2020/0061391 | A1* | 2/2020 | Krishnaswamy | A61N 5/1071 |
| 2021/0162241 | A1* | 6/2021 | Watts | H05H 7/001 |

FOREIGN PATENT DOCUMENTS

| | | |
|---|---|---|
| CN | 104637472 A | 5/2015 |
| CN | 105457171 A | 4/2016 |
| CN | 105833431 A | 8/2016 |

OTHER PUBLICATIONS

Written Opinion in corresponding PCT application No. PCT/AU2019/050519, Jul. 26, 2019, 7 pp.
International Preliminary Report on Patentability in corresponding PCT application No. PCT/AU2019/050519, Sep. 2, 2020, 96 pp.
Office Action issued in related application CN201980048588.9, Oct. 26, 2022, 6 pp.
Best available translation of Oct. 26, 2022, Office Action issued in related application CN201980048588.9, 4 pp.
Machine translation of CN105457171A Abstract, pp. 1.
Machine translation of CN105457171A Description pp. 10.
Machine translation of CN105833431A Abstract, pp. 1.
Machine translation of CN105833431A Description pp. 12.
Machine translation of CN1870940A Abstract, pp. 2.
Machine translation of CN1870940A Description pp. 12.
Machine translation of CN101810910A Abstract, pp. 1.
Machine translation of CN101810910A Description pp. 8.
Machine translation of CN104637472A Abstract, pp. 1.
Machine translation of CN104637472A Description pp. 3.
Extended European Serch Report in related application No. EP 19807318.1, Mar. 14, 2022, 8 pp.

* cited by examiner

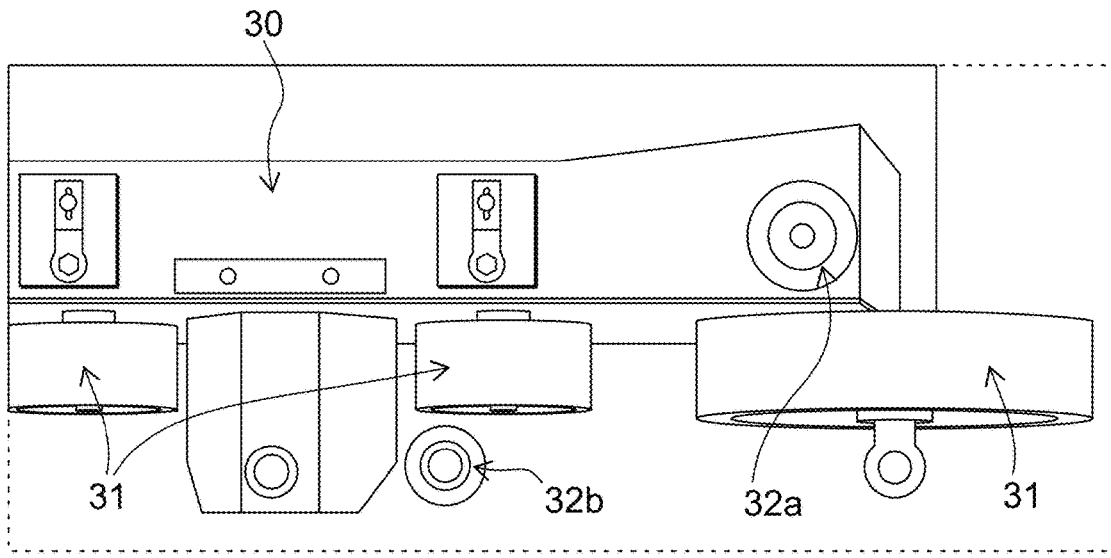
FIG. 4
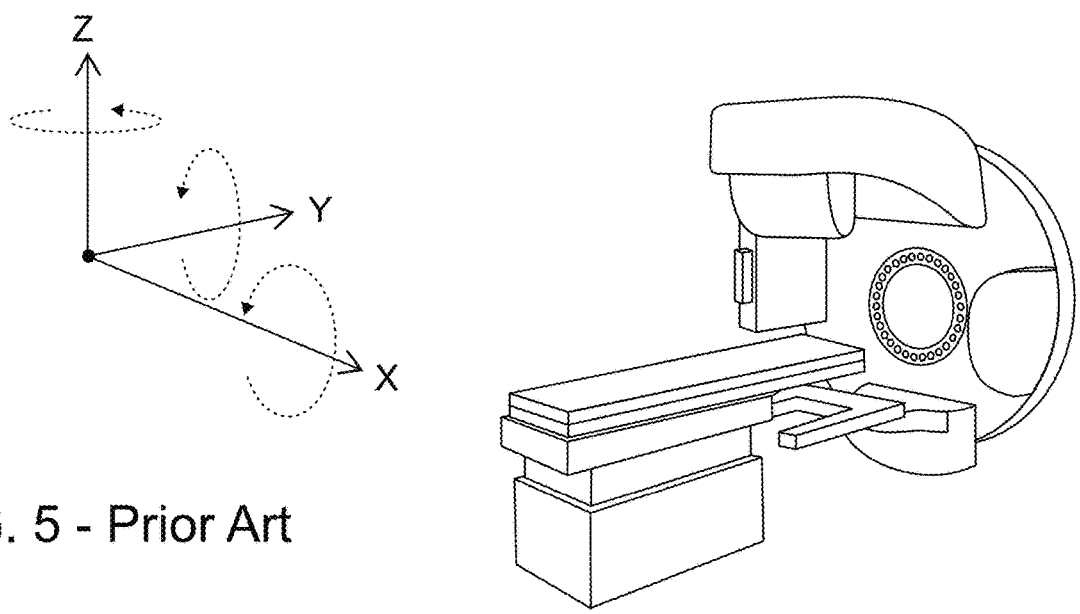
FIG. 5 - Prior Art

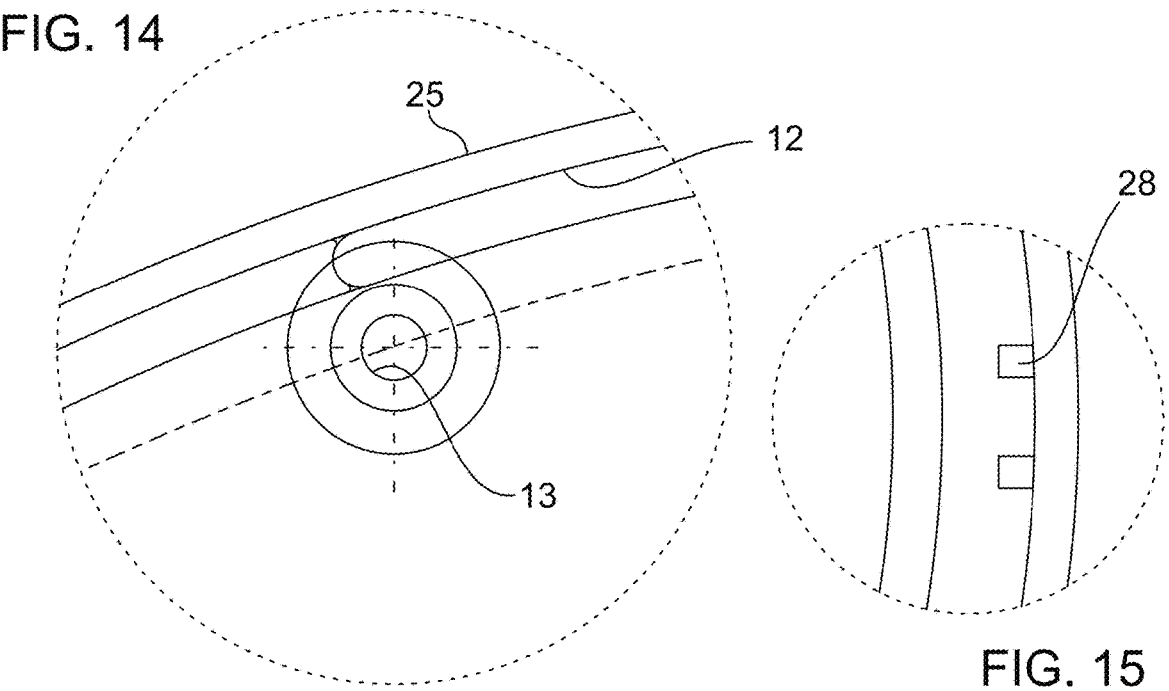
FIG. 14
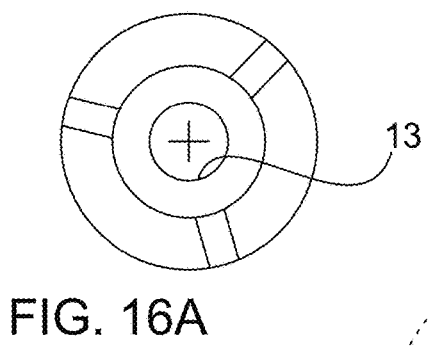
FIG. 16A
FIG. 15
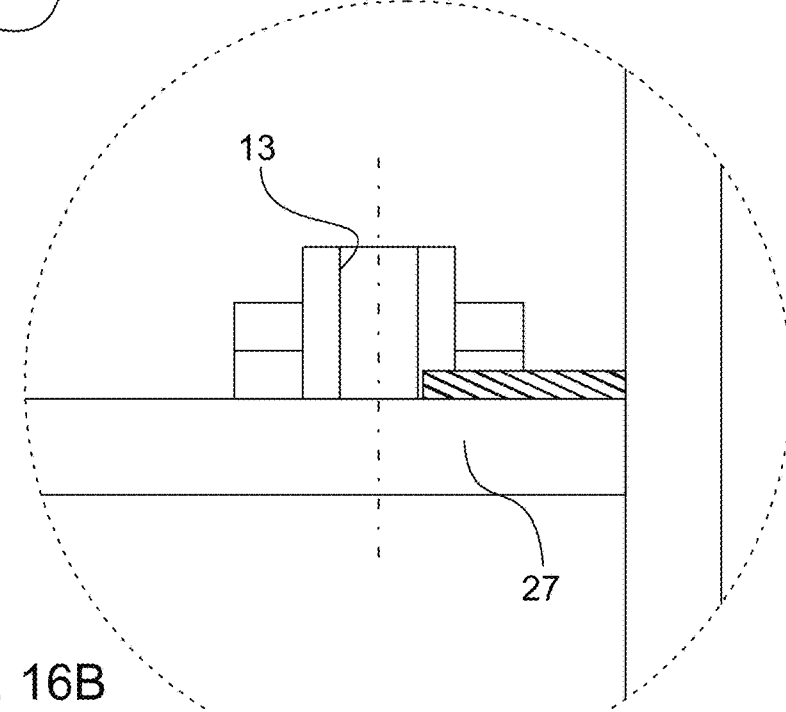
FIG. 16B

TO LINEAR ACCELERATORS

FIELD OF THE INVENTION

The present invention relates to improvements in linear accelerators ("LINAC"). In particular, the present invention relates to modifications to linear accelerators to improve the isocentric accuracy of the linear accelerator.

BACKGROUND OF THE INVENTION

Radiotherapy refers to a regime of treatments which involve exposing cancer cells to intense X-ray radiation. The desired outcome of these treatments is that cancer cells will be damaged beyond repair ("killed"), and will therefore be unable to further reproduce within the patient's body. A linear accelerator is the device most commonly used for external beam radiation treatments for patients with cancer. The linear accelerator can be used to treat all parts or organs of the body, and functions by delivering high-energy X-rays to the region of the patient's tumour.

Typically, however, cancerous growths are embedded within healthy tissue. As a result, some of the healthy tissue is also damaged during the treatment of the cancer cells, as the radiation must pass through the healthy tissue in order to reach the cancerous cells or tumour.

Depending on the sensitivity of the surrounding tissue, the effect of damage to healthy tissue from the treatment of the cancer ranges from minimal to life-threatening. For example, treatments close to the brain, spinal cord, optic nerve, lung, kidneys, liver, reproductive organs, eyes, prostate gland, bladder and rectum have potentially serious implications if the nearby organs are not adequately protected from exposure to the damaging radiation. In some patients, exposure of healthy tissue to radiation may also lead to the formation of secondary cancers. As a result of the radiation treatment the primary cancer should be killed, however, any damage to surrounding tissues, or formation of secondary cancers is clearly highly undesirable. The patient should be able to be treated successfully, without causing damage to tissues other than the tumour, and without an increased risk of further cancer formation.

It is of great importance, therefore, not only to make use of a beam of radiation which can be accurately shaped, but also to provide a mechanically stable platform for the radiation beam in order to provide pinpoint accuracy in three dimensions, up/down, forwards/backwards, and sideways.

In a LINAC, all moving and rotating parts are centred about a single point in space. This point in space, relative to the treatment machine and about which various components of the LINAC rotate, is referred to as the "isocentre". The composite parts of the LINAC are mechanically adjusted during installation, to minimise the volume of the isocentre, which is a result of these mechanical alignments and the positioning of the LINAC as required for patient treatment and any mechanical forces active on the structure of the treatment unit, that may also act to distort the intended positioning. The location and volume of the radiation isocentre plays a critical role in treatment planning as the radiation beam needs to be accurately located with respect to the centre of the target tumour, and any surrounding critical organs at risk. The intention is, of course, to target and kill tumour cells and minimise damage to healthy tissues. A smaller volume isocentre creates greater accuracy of the radiation isocentre, which is paramount to improve patient treatments and results.

Since most linear accelerators weigh approximately 7 to 8 tonnes, some distortion of the isocentre occurs due to the weight of equipment in association with the required movements and rotations. The distortion is typically caused by sagging in the arm, plus wear in any associated bearings and means that the accuracy of the radiation isocentre may be decreased, thereby increasing the chance of damage to healthy tissue surrounding the tumour. As equipment ages and is used repeatedly, the likelihood of some sagging is increased, and thereby the likelihood of some inaccuracy in the radiation isocentre increases over time.

Specifically, distortion of the isocentre can occur in three directions: the X axis, the Y axis and the Z axis (as shown in FIG. 5 PRIOR ART) of the linear accelerator. As would be understood, the X axis is a horizontal axis that extends perpendicular to the direction from which the arm extends from the linear accelerator, the Y axis is a horizontal axis that extends parallel to the direction from which the arm extends from the linear accelerator, while the Z axis is a vertical axis that extends perpendicular to the direction from which the arm extends from the linear accelerator.

In some LINACs, the diameter of the isocentre volume may be greater than 1.5 millimetres due to these unintended distortions, meaning that the effectiveness of providing pinpoint accuracy in the targeting of cancer cells is dramatically reduced.

There would, therefore, be a clear and beneficial advantage if it were possible to improve the isocentric accuracy of a LINAC, so as to more accurately target a patient's tumour, while minimising the damage to the surrounding healthy tissue. The inventor has conducted dedicated research and development over the preceding years, seeking to address the serious problem of isocentre distortion, due to sagging of LINAC support structures. Until now no suitable method to address the problem has been found. The invention is a significant and surprising improvement over the prior art, which is likely to be universally adopted by the industry, both for new equipment and for existing equipment. Through use of the invention the isocentre accuracy is dramatically improved, leading to less damage of healthy tissue and a reduction in the risk of damaged healthy tissues leading to secondary cancer development. All in all the outcome for the patient should be improved through use of the invention, in an easy to use and economic to produce apparatus when considering the significant patient benefit.

It will be clearly understood that, if a prior art publication is referred to herein, this reference does not constitute an admission that the publication forms part of the common general knowledge in the art in Australia or in any other country. In general terms, the present invention is directed to improvements to linear accelerators, which may at least partially overcome at least one of the abovementioned disadvantages or provide the consumer with a useful or commercial choice.

It is an object of the present invention to provide an improvement to a linear accelerator that at least ameliorates one or more of the aforementioned problems of the prior art.

DISCLOSURE OF THE INVENTION

The present invention, in one form, resides broadly in a drum assembly for a linear accelerator, the drum assembly comprising a drum having a front face including a front rim and a rear face including a rear rim, one or more support wheels supporting the drum, an arm extending from the front face of the drum and including a beam collimator through which a beam of radiation is emitted to form a radiation isocentre and one or more rear rim members associated with the rear rim, the rear rim members being adapted to substantially offset distortion to the isocentre due to unintended movement of the drum assembly.

The present invention, in one form, resides broadly in a drum assembly for a linear accelerator, the drum assembly comprising a drum having a front face including a front rim and a rear face including a rear rim, one or more support wheels supporting the drum, an arm extending from the front face of the drum and including a beam collimator through which a beam of radiation is emitted to form a radiation isocentre and one or more rear rim members associated with the rear rim, the rear rim members being adapted to substantially offset distortion to the isocentre in the Y direction due to unintended sagging of the beam arm which occurs with rotation of the drum assembly.

The present invention, in one form, resides broadly in a drum assembly for a linear accelerator, the drum assembly comprising a drum having a front face including a front rim and a rear face including a rear rim, one or more support wheels supporting the drum, an arm extending from the front face of the drum and including a beam collimator through which a beam of radiation is emitted to form a radiation isocentre and one or more front rim members associated with the front rim, the front rim members being adapted to substantially offset sagging of the arm.

The present invention, in one form, resides broadly in a drum assembly for a linear accelerator, the drum assembly comprising a drum having a front face including a front rim and a rear face including a rear rim, one or more support wheels supporting the drum, an arm extending from the front face of the drum and including a beam collimator through which a beam of radiation is emitted to form a radiation isocentre and one or more front rim members associated with the front rim, the front rim members being adapted to substantially offset distortion to the isocentre in the Z direction due to unintended sagging and twisting of the beam arm which occurs with rotation of the drum assembly.

Preferably, the front rim members may also be adapted to substantially offset a distortion of the isocentre associated with sagging of the arm.

Accordingly, the present invention provides a drum assembly for a linear accelerator, the drum assembly comprising a drum having a front face including a front rim and a rear face including a rear rim, one or more support wheels supporting the drum, an arm extending from the front face of the drum and including a beam collimator through which a beam of radiation is emitted to form a radiation isocentre and one or more rear rim members associated with the rear rim, the inner surface of the rear rim members being provided with one or more projections extending therefrom, that extend between the rear rim members and the inside edge of the rear rim, and the rear rim members and projections being adapted to substantially offset distortion to the isocentre due to unintended movement of the drum assembly and further wherein the drum assembly also comprises one or more locating members associated with the rear rim, and the rear rim members and locating members together are adapted to create and or limit movement of the drum assembly in a direction that is substantially parallel to the axis of rotation of the drum assembly (i.e. in the direction of the Y axis) the created movement of the drum assembly will substantially offset the equal and opposite distortion of the isocentre caused by the deflection of the beam arm, at particular gantry angles.

Accordingly, the invention provides in a variant, a drum assembly for a linear accelerator, the drum assembly comprising a drum having a front face including a front rim and a rear face including a rear rim, one or more support wheels supporting the drum, an arm extending from the front face of the drum and including a beam collimator through which a beam of radiation is emitted to form a radiation isocentre and one or more rear rim members associated with the rear rim, the inner surface of the rear rim members being provided with one or more projections extending therefrom, that extend between the rear rim members and the inside edge of the rear rim, and the rear rim members and projections being adapted to substantially offset distortion to the isocentre due to unintended movement of the drum assembly.

The drum may be of any suitable shape, size and configuration. For instance, the drum may have a square, triangular, circular, oval or rectangular cross-sectional shape. Preferably, however, the drum may be substantially circular in cross-section and substantially cylindrical in shape. In a preferred embodiment of the invention, the drum may be oriented so that the front and rear faces of the drum are positioned substantially vertically in use. It will be understood that the term "front face" in reference to the drum is intended to indicate the face of the drum from which the wave accelerator, X-ray target and beam collimator extend, while the term "rear face" is intended to indicate the opposite side of the drum to that from which the wave accelerator extends and where the electron gun is located.

As previously stated, the front face of the drum includes a front rim, while the rear face of the drum includes a rear rim. The front and rear rims may simply comprise an edge of the front and rear faces. Alternatively, the front and rear faces may be provided with one or more lip members at the outer edges thereof that extend at least partially about the circumference of the front and rear faces. A skilled addressee will understand, however, that the exact nature of the front rim and the rear rim is not critical to the invention.

The one or more support wheels may be of any suitable form, and may be positioned in any suitable orientation relative to the drum. For instance, the support wheels may be positioned substantially vertically so that the axis of rotation of the support wheels is substantially parallel to the axis of rotation of the drum. Alternatively, the support wheel may be positioned substantially horizontally so that the axis of rotation of the support wheels is substantially perpendicular to the axis of rotation of the drum. In other embodiments of the invention, a combination of vertical and horizontal support wheels may be provided.

It will be understood that the purpose of the vertical support wheels is to support the drum and facilitate rotation of the drum about a horizontal axis (the Y axis), while the horizontal support wheels act to limit the movement of the gantry drum across the surface of the vertical support wheels (movement along the Y axis). Preferably, the purpose of any vertical support wheels is to support the drum and facilitate rotation of the drum about a horizontal axis (the Y axis), while any horizontal support wheels act to limit the movement of the gantry drum across the surface of the vertical support wheels. This may assist in maintaining the drum in an essentially fixed position in the direction of the Y axis. The support wheels are conventional within the present art and no further description of the support wheels is required. It is worth noting, however, that, in conventional LINACs, the front and rear rims of the drum are in abutment with the support wheels such that rotation of the drum assembly causes rotation of the support wheels and vice versa. Thus, in the present invention, the front rim members (and rear rim members as described later) are in contact with the support wheels and are positioned between the support wheels and the respective rims.

It is envisaged that the drum assembly may comprise a base portion to which the support wheels may be mounted. It is envisaged that the vertical support wheels may be mounted to the base portion in a vertical position (such as to a side or edge of the base portion), while the horizontal support wheels may be mounted in a horizontal position (such as to an upper or lower surface of the base portion).

The one or more front rim members may be of any suitable size, shape or configuration. In some embodiments of the invention, the one or more front rim members may extend at least partially about the circumference of the front rim. Alternatively, however, the one or more front rim members extend substantially about the entire circumference of the front rim.

In some embodiments of the invention, one front rim member may be present. More preferably, however, two or more front rim members are present. The two or more front rim members may be of the same dimensions as one another, or may be of different dimensions in that each front rim member extends for a different length about the circumference of the front rim. Preferably, the total length of the two or more front rim members is less than the circumference of the front rim, although it is envisaged that the total length of the two or more front rim members may be substantially equal to the circumference of the front rim. It is envisaged that, when two or more front rim members are present where the total length of the front rim members is less than the circumference of the front rim, one or more gaps between front rim members may be formed about the circumference of the front rim.

Preferably, each of the front rim members defines an arc of a circle having a diameter substantially equal to, or slightly larger than, that of the front face.

In a most preferred embodiment of the invention, a pair of front rim members may be provided on the front rim. Preferably, the length of the pair of front rim members is such that the front rim members together extend about approximately 50 percent of the circumference of the front rim.

It is envisaged that, in embodiments of the invention in which a pair of front rim members is present, the front rim members may be spaced apart from one another around the circumference of the front rim. The front rim members may be spaced apart from another at any suitable distance. Preferably, however, the pair of front rim members are spaced apart approximately 180 degrees from one another about the circumference of the front rim.

The pair of front rim members may be located at any suitable location on the rim relative to the arm. Preferably, however, the front rim members are spaced approximately 90 degrees about the circumference of the front rim from the arm (or at least the closest point on the front rim to the location of the arm). In this way, when the beam of radiation issues from the arm in a substantially horizontal position, sagging of the arm (and therefore distortion of the isocentre) may be substantially precluded due to the positioning of one of the pair of front rim members in a lower region of the drum (i.e. located at least partially between the support wheel and the front rim).

By locating the front rim members at this point, the effect of gravity on the drum assembly (which causes sagging of the arm and distortion of the isocentre) may be offset such that the volume of the isocentre is substantially minimised.

In a preferred embodiment of the invention, the front rim members may be provided with inner and outer surfaces, with the inner surface of the front rim members being located in abutment with, or in close proximity to, the front rim.

In some embodiments of the invention, the thickness of the front rim members may be substantially constant along their entire length. Alternatively, the thickness of the front rim members may vary along their length. In this embodiment of the invention, the inner and/or upper surface of the front rim members may be provided with one or more peaks and/or troughs such that the thickness of the front rim members changes along its length. By providing one or more peaks and/or troughs on the front rim members, a substantially constant distance between the support wheels and the front rim may be maintained, and the likelihood of compression of the front rim members by the weight of the drum may be minimised. In other embodiments of the invention, two or more front rim members may be located so as to at least partially overlap one another, thereby increasing the strength and further reducing the effect of sagging of the arm.

It is envisaged that, in some embodiments, the inner surface of the front rim members may be provided with one or more projections extending therefrom. The one or more projections may be of any suitable size, shape and configuration, and may extend from the inner surface of the front rim members at any suitable angle. Preferably, however, the one or more projections extend between the inner surface of the front rim members and the front rim such that the one or more projections abut the front rim in use so as to support the front rim members and fix them in position on the flat face of the front rim.

Any suitable number of projections may be provided, although it is envisaged that a plurality of projections spaced about the circumference of the front rim may be provided. The projections may be spaced at any suitable intervals, and may be spaced evenly about the circumference of the front rim or may be spaced apart at varying intervals.

In some embodiments of the invention, the front rim members may extend outwardly beyond the front face of the drum. In this embodiment of the invention, the front rim members may be provided with one or more projections that extend between the front rim members and the front face of the drum. In this way, the front rim members may be substantially fixed in position around the flat face of the front rim.

The front rim members may be associated with the front rim in any suitable manner. For instance, the front rim members may be attached to the front rim using one or more fasteners. Any suitable fasteners may be provided, such as mechanical fasteners including one or more nails, bolts, rivets, screws or the like, or any combination thereof, or chemical fasteners such as an adhesive. Alternatively, the front rim members may be connected to the front rim using a frictional fitting, one or more loops, ties, hooks, hook and loop fasteners (e.g. Velcro) or the like, or any combination thereof. In other embodiments, the front rim members may be connected to the front rim using a snap fitting.

In alternative embodiments of the invention, the front rim members may be fixedly connected to the front rim, such as by welding, brazing or any other suitable technique. Still further, the front rim members may be integrally formed with the front rim of the drum.

The front rim members may be fabricated from any suitable material. Preferably, however, the front rim members may be fabricated from a material capable of withstanding being crushed by the weight of the drum when in use. Thus, in a preferred embodiment of the invention, the front rim members may be fabricated at least partially from a metal, such as steel, titanium (or alloys thereof) or the like. By fabricating the front rim members from a material capable of withstanding being crushed by the weight of the drum, sagging of the LINAC, (and therefore distortion of the isocentre) may be reduced or even eliminated. Thus, it is envisaged that the front rim members may act as shims.

In some embodiments of the invention, the drum assembly may further comprise one or more rear rim members. It is envisaged that the rear rim members may be associated with the rear rim using any suitable technique. For instance, the rear rim members may be attached to the rear rim using one or more fasteners. Any suitable fasteners may be provided, such as mechanical fasteners including one or more nails, bolts, rivets, screws or the like, or any combination thereof, or chemical fasteners such as an adhesive. Alternatively, the rear rim members may be connected to the rear rim using a frictional fitting, one or more loops, ties, hooks, hook and loop fasteners (e.g. Velcro) or the like, or any combination thereof. In other embodiments, the rear rim members may be connected to the rear rim using a snap fitting.

In alternative embodiments of the invention, the rear rim members may be fixedly connected to the rear rim, such as by welding, brazing or any other suitable technique. Still further, the rear rim members may be integrally formed with the rear rim of the drum.

The one or more rear rim members may be of any suitable size, shape or configuration. In some embodiments of the invention, the one or more rear rim members may extend at least partially about the circumference of the rear rim.

Alternatively, the one or more rear rim members may extend substantially about the entire circumference of the rear face of the rear rim.

In some embodiments of the invention, one rear rim member may be present. More preferably, however, two or more rear rim members are present. The two or more rear rim members may be of the same dimensions as one another, or may be of different dimensions in that each rear rim member extends for a different length about the circumference of the rear face of the rear rim.

Preferably, each of the rear rim members defines an arc of a circle having a diameter substantially equal to, or slightly larger than, that of the rear face.

In a most preferred embodiment of the invention, multiple rear rim members may be provided on the rear rim. Preferably, the length of the rear rim members is such that the rear rim members extend up to approximately 80 percent of the circumference of an edge of the rear rim.

The rear rim members may be located at any suitable location on the rim relative to the arm. Preferably, however, the rear rim members are spaced symmetrically around the lowest point of the rear rim when the drum is at zero degrees of rotation, and extend up to approximately 80 percent of the circumference of the rear edge of the rear rim. In this way, when the beam of radiation issues from the arm in a substantially vertical position, the axial movement (in the direction of the Y axis) of the drum is affected in such a way as to offset the sagging of the arm (and therefore distortion of the isocentre which is moved back towards the front face of the drum as a result of the typical sag in the arm at that angle).

By locating the rear rim members at this point, the effect of gravity on the arm (which causes distortion of the isocentre), may be offset such that volume of the isocentre is substantially minimised.

In a preferred embodiment of the invention, the rear rim members may be provided with inner and outer surfaces, with the inner surface of the rear rim members being located in abutment with, or in close proximity to, the rear edge of the rear rim.

Thus, in this embodiment of the invention, at least a portion of the rear rim members may be located on the rear face of the drum.

In some embodiments of the invention, the thickness of the rear rim members may be substantially constant along their entire length. Alternatively, the thickness of the rear rim members may vary along their length. In this embodiment of the invention, the inner and/or upper surface of the rear rim members may be provided with one or more peaks and/or troughs such that the thickness of the rear rim members changes along its length. In other embodiments of the invention, two or more rear rim members may be located so as to at least partially overlap one another, thereby increasing the strength and further reducing the likelihood of sagging of the arm.

It is envisaged that, in some embodiments, the inner surface of the rear rim members may be provided with one or more projections extending therefrom. The one or more projections may be of any suitable size, shape and configuration, and may extend from the inner surface of the rear rim members at any suitable angle. Preferably, however, the one or more projections extend between the inner surface of the rear rim members and the rear rim such that the one or more projections abut the rear rim in use so as to support the rear rim members in a fixed position.

Any suitable number of projections may be provided, although it is envisaged that a plurality of projections spaced about the circumference of the rear rim may be provided. The projections may be spaced at any suitable intervals, and may be spaced evenly about the circumference of the rear rim or may be spaced apart at varying intervals.

In some embodiments of the invention, the rear rim members may extend outwardly beyond the rear edge of the rear rim. In this embodiment of the invention, the rear rim members may be provided with one or more projections that extend between the rear rim members and the inside edge of the rear rim.

In some embodiments of the invention, the drum assembly may further comprise one or more locating members. Preferably, the one or more locating members may be associated with the rear rim. Thus, in embodiments of the invention in which rear rim members and locating members are both present, the rear rim members and locating members may together be adapted to create and/or limit movement of the drum assembly in a direction that is substantially parallel to the axis of rotation of the drum assembly (i.e. in the direction of the Y axis). This created movement will substantially offset the equal and opposite distortion of the isocentre caused by the deflection of the beam arm at particular gantry angles.

In a preferred embodiment, the one or locating members are positioned so as to act upon an inner edge of the rear rim. It will be understood that the term "inner edge of the rear rim" is intended to refer to the edge of the rear rim that is closest to the front rim of the drum. Thus, it is envisaged that the locating members may be positioned at least partially between the front and rear rims of the drum.

Preferably, the locating members act upon the rear rim such that a force is applied to the rear rim to control and/or limit forward movement of the drum assembly (i.e. in the direction of the Y axis). The locating members may be of any suitable size, shape or configuration, and may include one or more blocks adapted to be located in abutment with the inner edge of the rear rim so as to limit forward movement of the drum assembly to the thickness of the rear rim members on the rear edge of the rear rim.

In an alternative embodiment of the invention, the locating members may include one or more locating wheels located in abutment with, or in close proximity to, the inner edge of the rear rim. The locating wheels may act in concert with the horizontal support wheels to support the drum. Preferably, however, the locating wheels may be biased into position using one or more biasing members (or may be associated with one or more biasing members), such that the drum is substantially unable to overcome the bias of the biasing members and unintended forward movement of the drum is reduced or eliminated.

Any suitable biasing member may be used, such as, but not limited to, one or more springs or spring-loaded plates, discs or the like. In this embodiment of the invention, the biasing member may be located between the locating wheels and the rear rim such that the drum assembly is unable to overcome the bias of the biasing members, and therefore unintended forward movement of the drum assembly is substantially precluded.

Alternatively, the biasing member may include one or more elongate members that bias the locating wheels into abutment with (or close proximity to) the rear rim. Preferably the one or more elongate members are spring-loaded. Thus, while the inner edge of the rear rim may contact the locating wheels, the drum is unable to overcome the bias of the elongate members and unintended forward movement of the drum assembly may be substantially precluded.

Preferably the elongate members comprise a first end associated with the locating wheels and an opposed fixed second end. The elongate members may be of any suitable length, cross-sectional, shape and so on.

In a preferred embodiment of the invention, the drum assembly of the present invention produces an isocentre of less than about 1 millimetres. More preferably, the drum assembly of the present invention produces an isocentre of less than about 0.5 millimetres.

In another aspect, the invention resides broadly in in a drum assembly for a linear accelerator, the drum assembly comprising a drum having a front face including a front rim and a rear face including a rear rim, one or more support wheels supporting the drum, an arm extending from the front face of the drum and including a beam collimator through which a beam of radiation is emitted to form an isocentre, and one or more rear rim members associated with the rear rim, and one or more locating members associated with the rear rim, the rear rim members and the locating members together being adapted to substantially offset deflection and/or movement of the beam collimator.

Preferably, the rear rim members and the locating members may also be adapted to substantially offset and reduce the volume of the isocentre associated with deflection and/or movement of the beam collimator.

In another aspect the invention resides broadly in a drum assembly for a linear accelerator, the drum assembly comprising a drum having a front face including a front rim and a rear face including a rear rim, one or more support wheels supporting the drum, an arm extending from the front face of the drum and including a beam collimator through which a beam of radiation is emitted to form an isocentre, and one or more front rim members associated with the front rim, one or more rear rim members associated with the rear rim, and one or more locating members associated with the rear rim, the front rim members, the rear rim members and the locating members together being adapted to substantially offset sagging of the arm and deflection and/or movement of the beam collimator.

Preferably, the front rim members, the rear rim members and the locating members may also be adapted to substantially offset and reduce the volume of the isocentre associated with deflection and/or movement of the beam collimator and/or movement of the beam collimator.

The present invention provides numerous advantages over the prior art. For instance, the presence of the front rim members offsets sag in the arm predominantly when the arm is in a horizontal position, and the associated distortion of the isocentre. Similarly, the presence of the rear rim members and/or the locating members offsets currently experienced isocentre (focal point) movement in the direction of the Y axis as the drum rotates, and thereby reduces the associated volume of the isocentre.

The advantage of reducing or eliminating the volume of the isocentre of a LINAC is that treatment plans for a patient may be more precise, and may allow for a more intense dose of radiation to the tumour without causing damage to the surrounding healthy tissue. This increases the likelihood of successfully treating the tumour and returning the patient to a healthy, productive life.

It is envisaged that the present invention may reduce the volume of the isocentre from current sizes of 1.5 millimetres or more to isocentres of less than 1 millimetre, and more preferably less than 0.5 millimetres.

Any of the features described herein can be combined in any combination with any one or more of the other features described herein within the scope of the invention.

The reference to any prior art in this specification is not, and should not be taken as an acknowledgement or any form of suggestion that the prior art forms part of the common general knowledge.

INDUSTRIAL APPLICABILITY

The invention may be applied industrially, through manufacture of improvements to linear accelerators for supply to organisations or suppliers in need of the equipment. The improvements may be incorporated into the linear accelerator at the time of manufacture, or provided as a separate assembly to be provided with new equipment or retrofitted to existing equipment.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Disclosure of the Invention in any way. The Detailed Description will make reference to a number of drawings as follows:

FIG. 4 illustrates a plan view of a portion of a drum assembly according to an embodiment of the present invention;

FIG. 5 illustrates the direction of the axes of a linear accelerator (PRIOR ART) as a useful reference;

FIG. 14 is a detailed view of the schematic view from the front of FIG. 11 with the detail of the position of the boss, on the rim member, inside the rim;

FIG. 15 is a detailed view of the blocks at the 3'Oclock position on FIG. 11; and FIGS. 16a and b, is a two part schematic diagram of the boss of FIGS. 11 and 14, from above and then separately, in plan view to show the boss support.

DESCRIPTION OF THE EMBODIMENTS

Figure 1:
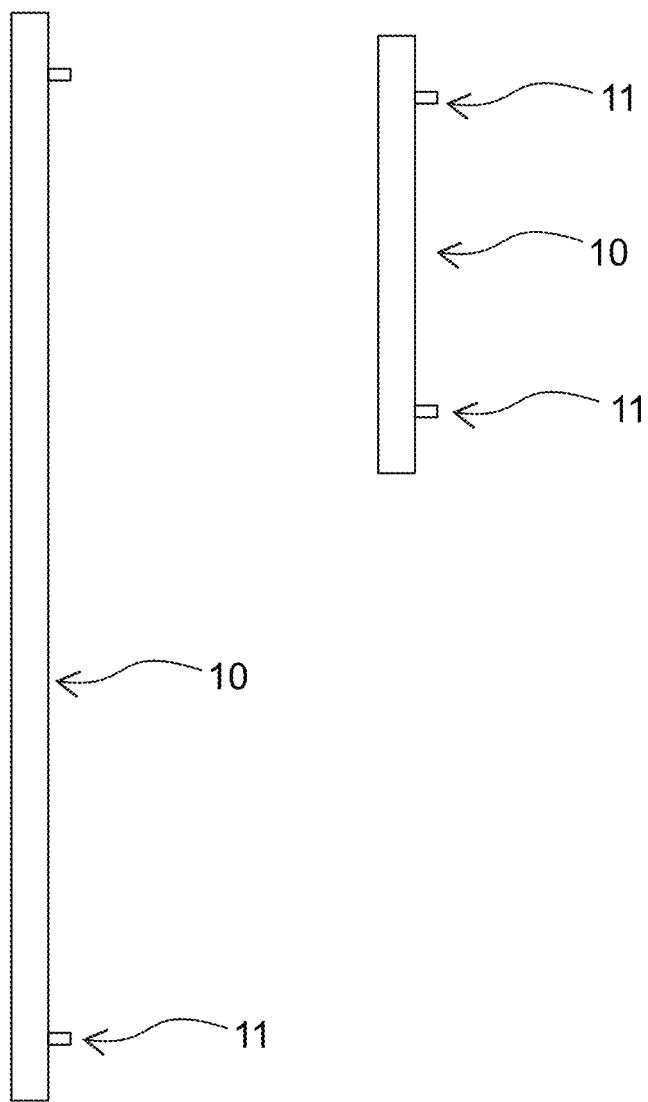
FIG. 1 illustrates a side view of front rim members according to an embodiment of the present invention.

With reference to FIGS. 1 to 4, embodiments of the invention are shown in various aspects, useful to the disclosure of the invention. With reference in particular to FIG. 1, there is illustrated a side view of front rim members 10 according to an embodiment of the present invention. In both FIGS. 1 and 2 the respective components are shown clearly, to illustrate the detailed features of the rim members, important to the working of the invention. Front rim members 10, each define an arc of a circle that is substantially the same diameter, or of a slightly larger diameter, to the diameter of the front rim of the drum assembly (neither shown in FIG. 1).

In the embodiment of the invention shown in FIG. 1, front rim members 10 together, have a circumference that is approximately equal to that of the front rim so that front rim members 10 could form a continuous rim about the front rim, if used together. Alternatively, only one of front rim members 10 could be used on the front rim so that the full circumference of the rim is not covered by front rim members 10. For instance, two of the smaller front rim members 10 could be used so that approximately 50 percent of the front rim is covered by front rim members 10.

Front rim members 10 are provided with a plurality of projections 11 that extend outwardly from front rim members 10, towards the front face (not shown in FIG. 1) of the drum assembly. In use, projections 11 will abut the front face of the drum assembly. Alternatively, projections 11 could be used to locate and or retain t front rim members 10 on the front rim.

Figure 2:
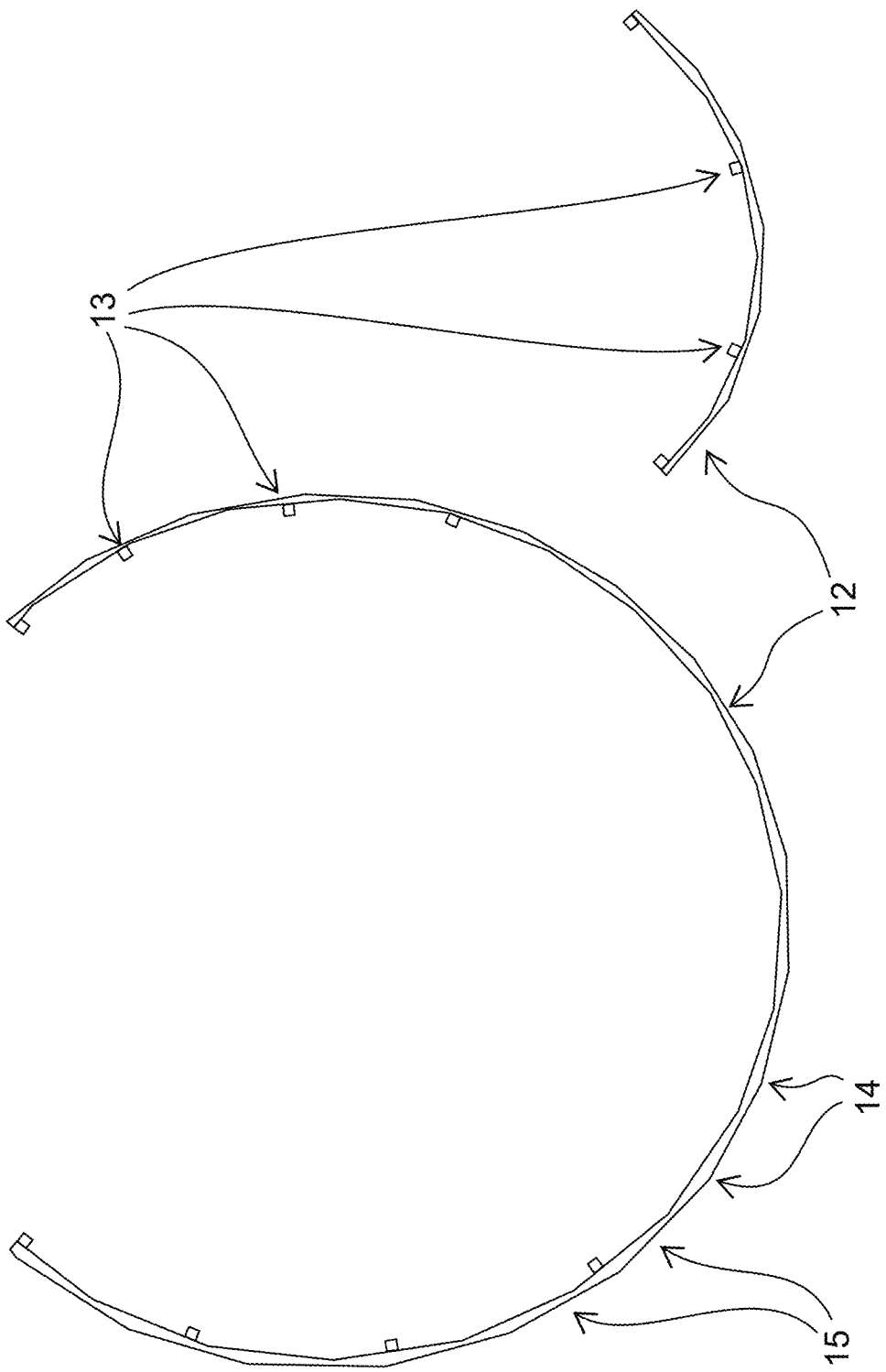
FIG. 2 illustrates a front view of rear rim members according to an embodiment of the present invention.

With reference in particular to FIG. 2, there is illustrated a front view of rear rim members 12 according to an embodiment of the present invention, similar to front rim members 10, as described above. Rear rim members 12 each define an arc of a circle that is substantially the same diameter, or of a slightly larger diameter, to the diameter of the rear rim of the drum assembly (neither shown in FIG. 2).

In the embodiment of the invention shown in FIG. 2, rear rim members 12, together have a circumference that is approximately equal to that of the rear rim (not shown in FIG. 2) so that rear rim members 12 could form a continuous rim about the rear rim, if used together. Alternatively, only one of rear rim members 12 could be used on the rear rim so that the full circumference of the rim is not covered by the rear rim members 12. For instance, two of the smaller rear rim members 12 could be used so that approximately 50 percent of the rear rim is covered by the rear rim members 12. Preferably, a rear rim member is located on the rear edge of the rear rim of the drum, as can be seen in FIG. 3.

Rear rim members 12 are provided with a plurality of projections 13 that extend inwardly from an inner surface of rear rim members 12 towards the rear rim of the drum assembly (neither shown in FIG. 2). In use, projections 13 will abut the rear rim (not shown) of the drum assembly. Alternatively, the projections 13 could be used to locate and/or retain the rear rim members 12 on the rear rim.

In FIG. 2 it may be seen that both inner and outer surfaces of rear rim members 12 are provided with a series of peaks 14 and troughs 15 that assist in preventing rear rim members 12 from being crushed by the weight of the drum (not shown).

Figure 3:
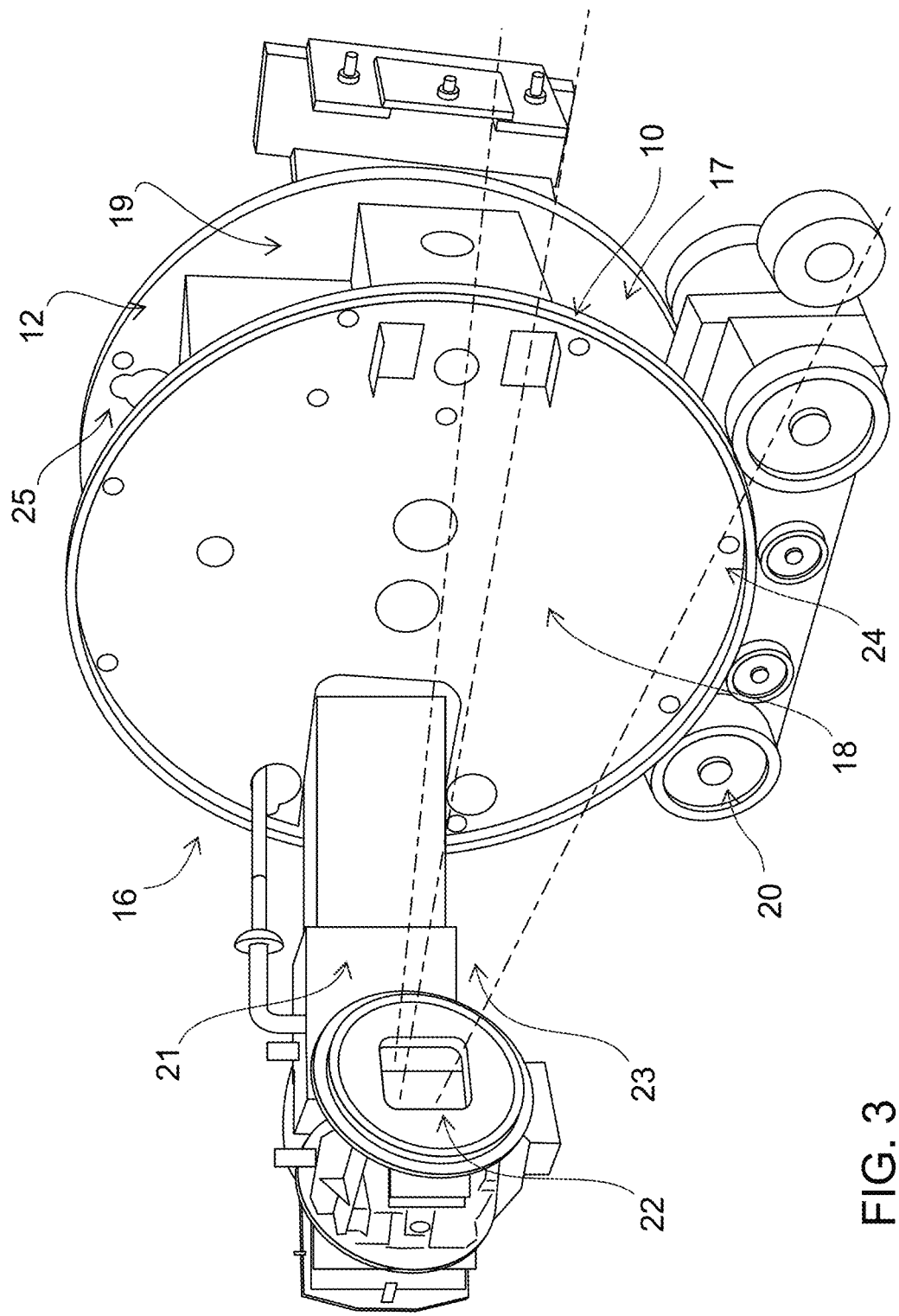
FIG. 3 illustrates an isometric view of a drum assembly according to an embodiment of the present invention, including the front and rear rim members of FIGS. 1 and 2.

With reference in particular to FIG. 3, there is illustrated an isometric view of drum assembly 16, according to an embodiment of the present invention. The view of FIG. 3 includes the front and rear rim components labelled 10, 11, 12 and 13 as described for FIGS. 1 and 2, as can be readily understood. In this Figure it may be seen that drum assembly 16 comprises drum 17 having front face 18, rear face 19 and a plurality of support wheels 20 atop which drum 17 rotates. In use, drum 17 rotates about a rotation of axis extending horizontally through the centre of both front face 18 and rear face 19 of drum 17. Drum 17 is positioned on its side so that the front face 18 and the rear face 19 are positioned substantially vertically, in use.

Extending from, or, more accurately, through, front face 18 is arm 21 housing a wave accelerator, an X-ray target (obscured) and beam collimator 22 from which beam of radiation 23 issues when the LINAC is in use. Beam of radiation 23 forms an isocentre about which drum assembly 16 rotates.

Front face 18 includes an annular front rim 24 that extends about the circumference of front face 18. Similarly, rear face 19 includes an annular rear rim 25 that extends about the circumference of rear face 19. In the embodiment of the invention shown in FIG. 3, front rim members 10 and rear rim members 12 are located on front rim 24 and rear rim 25, respectively, with rear rim members 12 located at least partially on rear face 19 of drum assembly 16. Front rim members 10 extend about a portion of the length of front rim 24, and therefore about a portion of the circumference of front face 18, while rear rim members 12 are located partly on rear face 19 of drum assembly 16, and extend onto the rear edge of rear rim 25. In this way, the rear rim members 12 extend about a portion of the circumference of the rear face 19.

Front rim members 10 are positioned so as to be located between front rim 24 and support wheels 20 as can be seen in FIG. 3; when arm 21 is positioned substantially horizontally. Front rim members 10 positioned between front rim 24 and support wheels 20 are adapted offset sagging of the arm 21 (i.e. movement in the direction of the Z axis) measured at the isocentre and therefore reduce distortion the isocentre volume, when arm 21 is positioned such that beam of radiation 23 is issued from beam collimator 22 in a substantially horizontal direction. Rear rim members 12 are positioned so as to prevent in-plane gantry movement of drum 17 along its axis of rotation (i.e. movement of the drum in the direction of the Y axis), which also would result in an increase in isocentre volume.

With reference in particular to FIG. 4 illustrates a plan view of a base portion 30 of a drum assembly according to an embodiment of the present invention. In this Figure, base portion 30 includes three vertical support wheels 31 on which the drum (not shown) is supported for rotation and two horizontal support wheels 32a, 32b, one of which 32a is fixed in position for use while the other 32b second is awaiting installation.

In use, the horizontal support wheels 32a, 32b are located in close proximity to an edge (and preferably a front edge) of the rear rim. In this way, the horizontal support wheels 32a, 32b control movement of the drum in the direction of the Y axis, thereby minimising the isocentre volume. The rear rim members may be located between the edge of the drum and the horizontal support wheels 32a, 32b to further prevent movement of the drum in the direction of the Y axis.

Use of the invention acts to control movement of the drum assembly in the direction of the Y and/or Z axes, in order to offset any movement in the location of the isocentre (and radiation isocentre), position, while the LINAC is in use. The different components act in such a way as to offset isocentre variations in separate axes caused mainly by the weight of the arm and gravitational forces at different gantry angles, plus to a lesser extent distortion and the weight and wear of the apparatus generally. The effect of these forces is to give rise to a predictable variation in the isocentre position, and by eliminating them through the offset produced by the additionally introduced members, the variations in isocentre position can be reduced and thereby the volume of the locus described by these positions is reduced and the accuracy of the isocentre is increased. As described elsewhere, even the smallest of inaccuracies in this regard can have unfortunate outcomes for the patient, losing healthy tissue unnecessarily, which may cause irreparable loss of function to organs, and clearly a degradation to the life of the patient in the short and longer term. The patient will be happy to have the tumour destroyed but will need to leave with the consequences of the treatment, if this involved loss of function through damage to healthy tissues. To avoid the inaccuracy, where very specific accuracy is possible through use of the same LINAC equipment, would be a hugely beneficial outcome of the invention. Use of the invention would remove the degradation of treatment through distortion to the isocentre over time as the LINAC equipment wears and ages through much repeated use. For new equipment, as the invention is likely to be fitted as standard, the accuracy and useful life of the equipment will be prolonged, a further beneficial outcome for the stakeholders, investing in this costly equipment for hospitals and other treatment centres.

The inventor has developed a clever and surprisingly useful invention, that works with LINAC apparatus to significantly improve the accuracy of the isocentre by acting against distortion due to sagging of the support assembly.

Figure 6:
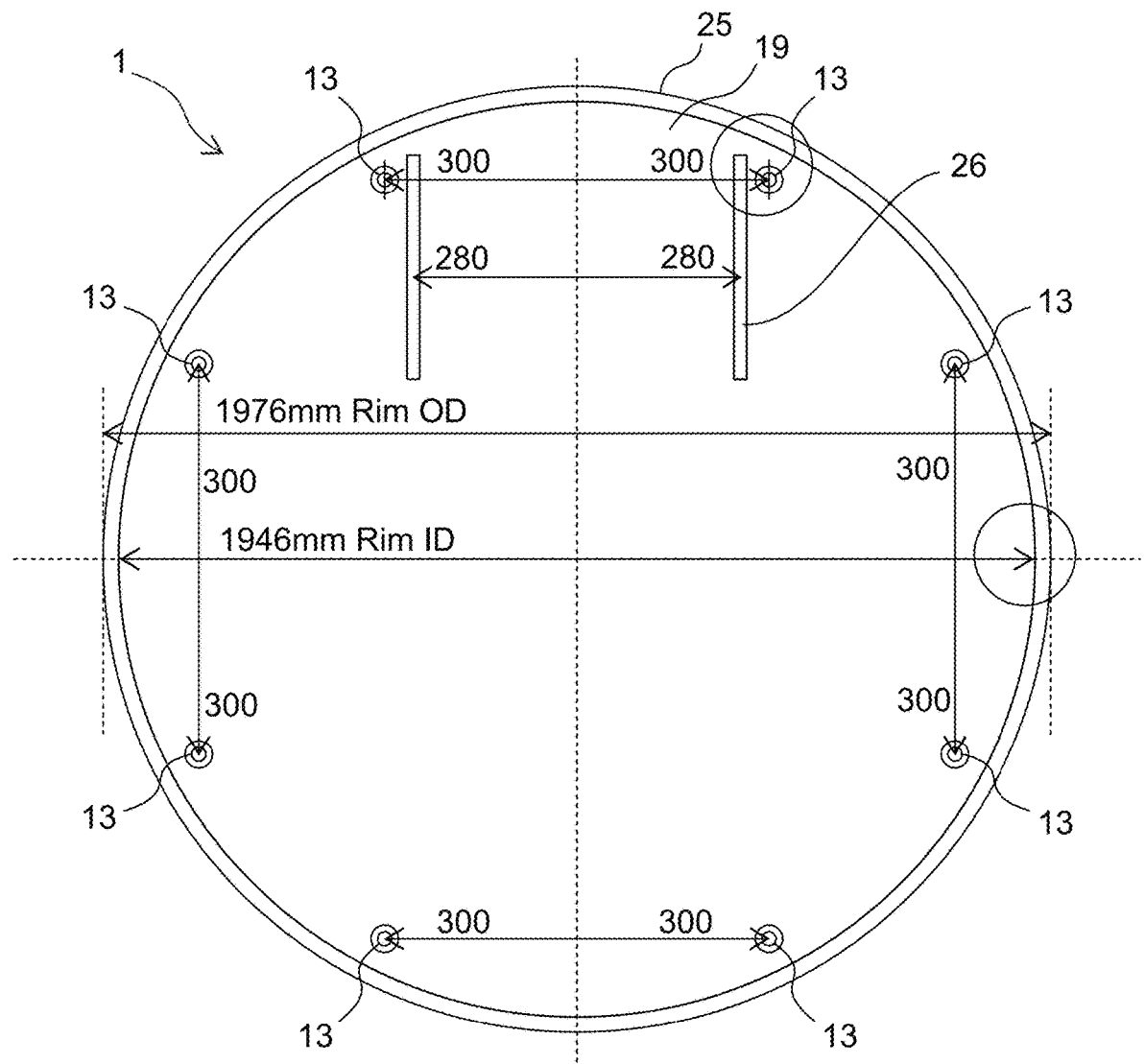
FIG. 6 illustrates a schematic partial view of a drum assembly variant to the first preferred embodiment, to highlight the rear rim members and projecting bosses in particular.

With reference to FIGS. 6 to 16, variants to the first embodiment are disclosed, in schematic form to show the best method of these aspects known—refer also the general description below. Various aspects are shown with much of the drum assembly and arm omitted, to assist illustration, and similar reference numerals are used throughout. In FIG. 6 annular rear rim 25 and the rear face to which rear rim members 12 and projecting bosses 13 are installed to provide support to the drum assembly against unintended movement. Annular front rim 24 with front rim bosses 11 (not shown) may be arranged in a similar, or slightly different arrangement, as appropriate. The rear rim arrangement is of great benefit to act against unintended movement in the apparatus that may increase isocentre volume.

As shown in FIG. 6, 8 projecting bosses 13 are shown within rim 26, in the position to which they will be arranged in use. The 8 bosses 13 have been found to be a particularly suitable arrangement. Bosses 13 are indicated in FIG. 6 are shown to indicate their actual position in use, spaced substantially evenly within rim 25, and rim members 12, rim members 12 being omitted form FIG. 6, for ease of illustration. An approximate horizontal or vertical spacing between neighbouring bosses 13 is shown as 300 millimetres. The outer dimension of rim 26 is shown as 1976 millimetres with an inner diameter 1946 millimetres as suitable for the particular drum assembly. Fitted with the inner rim of rear rim 26 and arranged circle of bosses 13 are rear rim members 12 which together substantially surround the inner circumference of rim 25. 8 sections are included of rear rim members to strongly support and surround the assembly, as has been found to be of particular use. Partial rim members may be include instead, but it is beneficial to include a plurality of rear rim members 12 to generally surround the inner surface of rim 25 and provide support thereto. A single rim member could be used around most or some of the inner circumference or this ring may be made of one or more overlapping section to create the strong support to the drum assembly.

The particular dimensions of these components may be readily adapted to the particular drum assembly as will be readily understood by the person skilled in the art. The arrangement of rim members 12 and bosses 13 is an illustrative example, in which 8 bosses are included spaced about the inner circumference, as indicated by the round circles. But more or less projections or bosses may be included and these may be spaced evenly to assist to distribute pressure or unevenly to suit the particular application.

Figure 7:
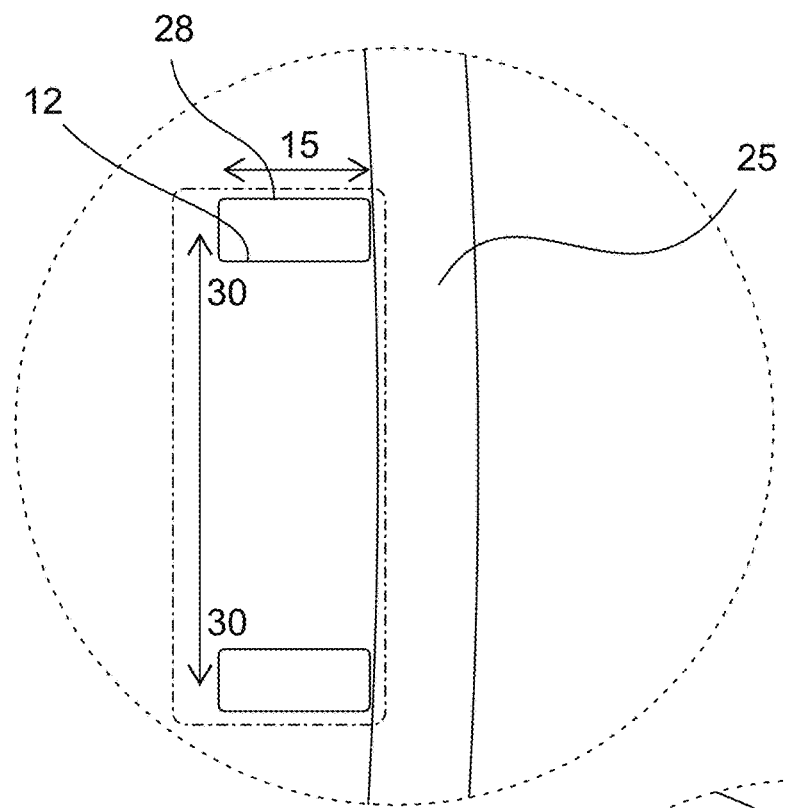
FIG. 7 illustrates the detailed view at the 3 O'clock position of FIG. 6 illustrating the cut-outs for LINAC apparatus.

Detailed image of part of FIG. 7 at the 3 O'clock position of FIG. 6, the detailed rebate to accommodate existing LINAC items, cut to be 60 by 15 millimetres in this example by 6 millimetres deep, as is self-explanatory.

Figure 8:
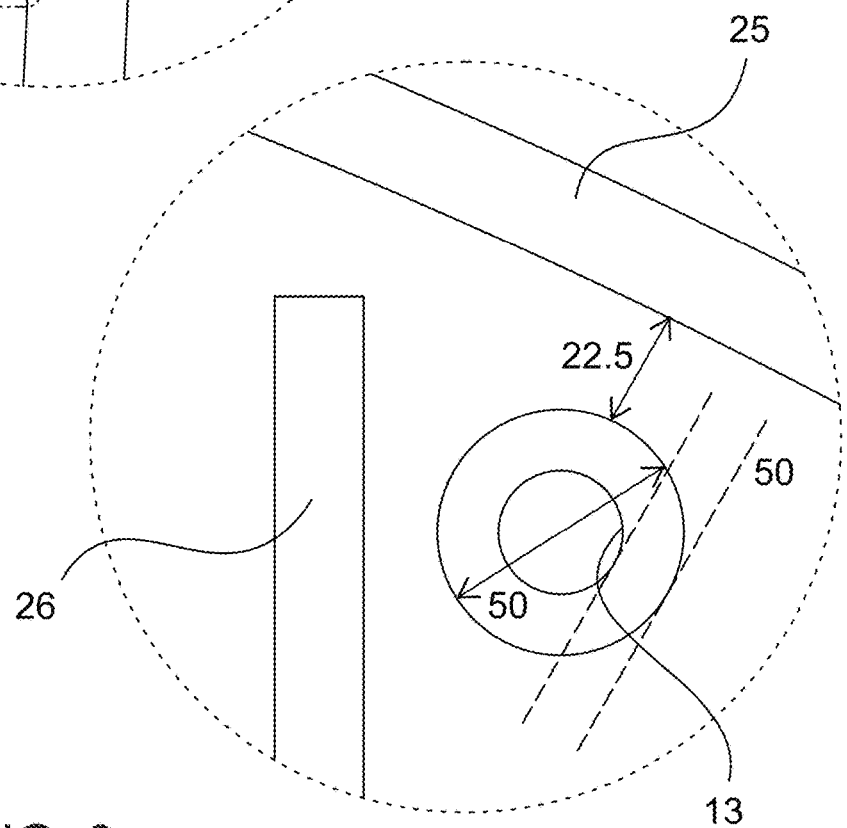
FIG. 8 illustrates the detailed view at the 1 O'clock position of FIG. 6 illustrating the boss and support.

Detailed image of part of FIG. 8 at the 1 O'clock position of FIG. 6, illustrates boss 13 and distance of inner diameter of the rim, relative to rim 25 and support 26. The detail of the boss, support and positions around the rim/rim members is given further below.

Figure 9:
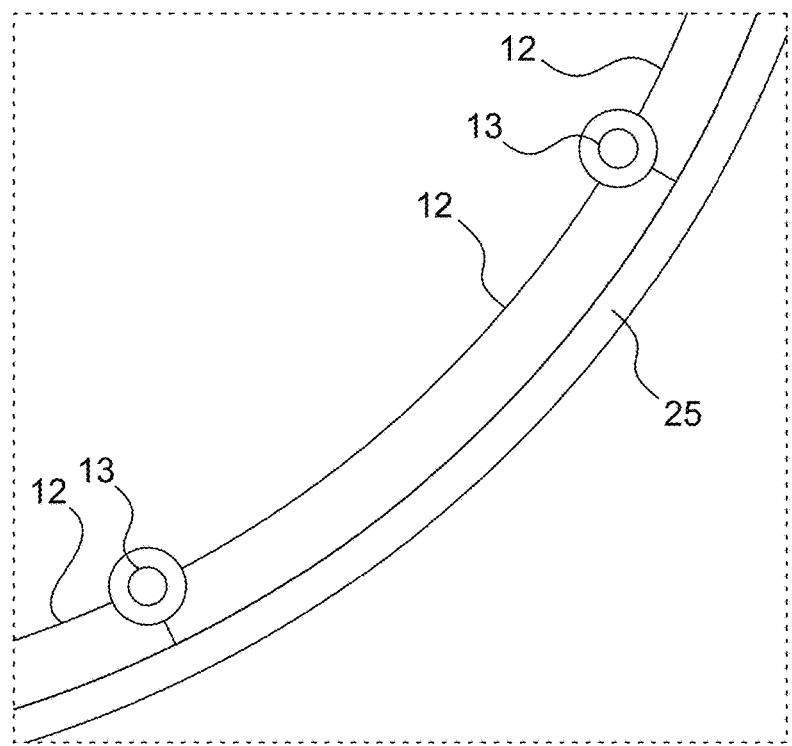
FIG. 9 illustrates a schematic partial view of the drum assembly of FIGS. 6 to 8 with the rim member in place between the rim and bosses.

With reference in particular to FIG. 9, an arc of rim 25 is shown, with rear rim members 12 between two bosses 13 positioned spaced about the arc. The defined 3 rear rim members 12 can be seen abutted one with the other and the two boss 13 sections. The inner surface of rim member 12 as shown has an outer circumference in the region of 1944 millimetres, within rim 25 to an inner dimension of 1880 millimetres. Bosses 13 are in close proximity to rear rim members 12. Again, clearly variation may be made to suit the particular application of these precise measurements but are given for illustrative purposes.

Figure 10:
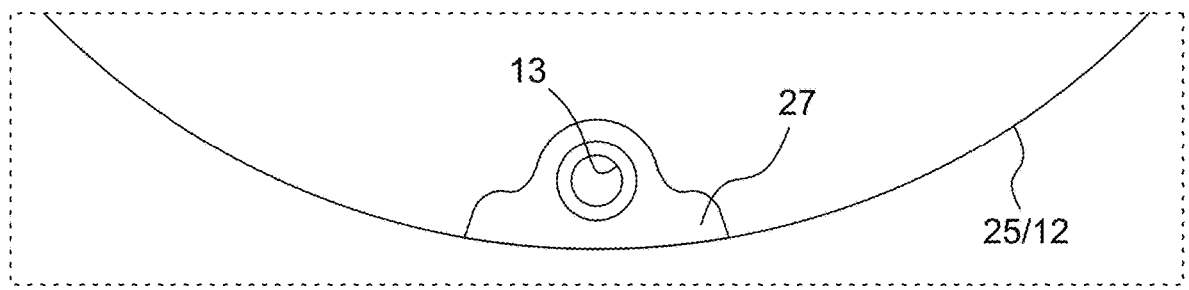
FIG. 10 illustrates a schematic partial view of the boss of FIGS. 6 to 9, with the detail shown including the boss support.

With reference to FIG. 10, boss 13 is shown with support 27 used to support boss 13 in its position and in its function to act against unintended movement.

Support 27 has a 22.5 millimetre width on either side of the aperture and an internal hole for a M4 grub screw. The width of boss support 27 can be seen to be approximately 160 millimetres (horizontal measurement across the arc) as suitable. There will be 8 boss 13 and corresponding 8 boss supports 27, in use.

8 Support segments as shown elsewhere are supported on top of 8 Boss Flanges FIG. 10, and two support segments join on each Boss flange. Boss flange 27 insertion on to Boss 13 is to be adjusted (then tightened with Grubb screws), to present flush face between face of Support Segments/rear rim members 12 and rim face 25, to allow for mounting of offset shims (not shown here). Shims to be locked in location by 8 addition clamping segments (not shown), which are tightened onto the shims by bolts through holes in the shims to sandwich the shims between the 8 Support Segments and the 8 Clamping segments.

Figure 11:
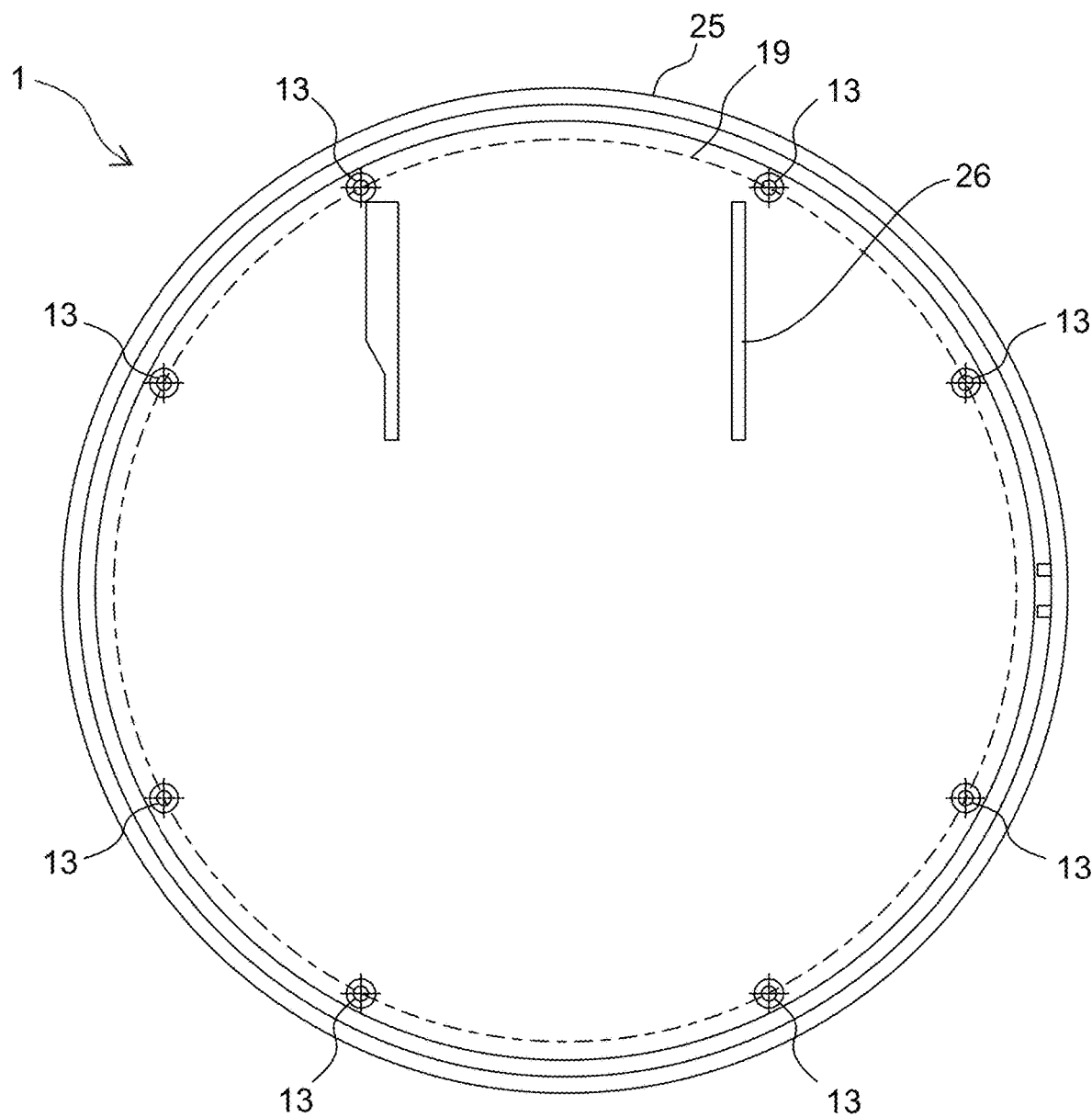
FIG. 11 illustrates a front view of the drum assembly of FIG. 6, indicating the rim and including the rim members and 8 bosses positioned about the inner circumference.
Figure 12:
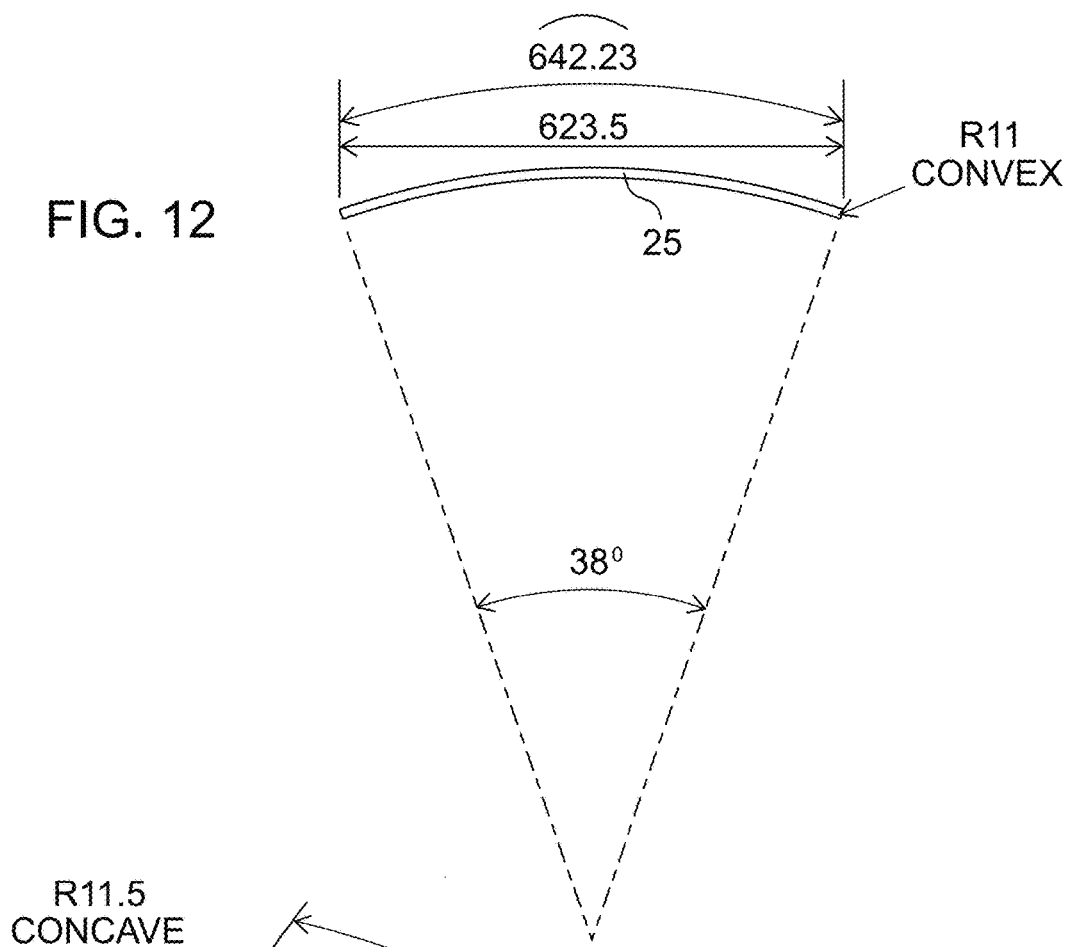
FIG. 12 indicates a first section of the rim of FIG. 11 with an arc of 38 degrees.
Figure 13:
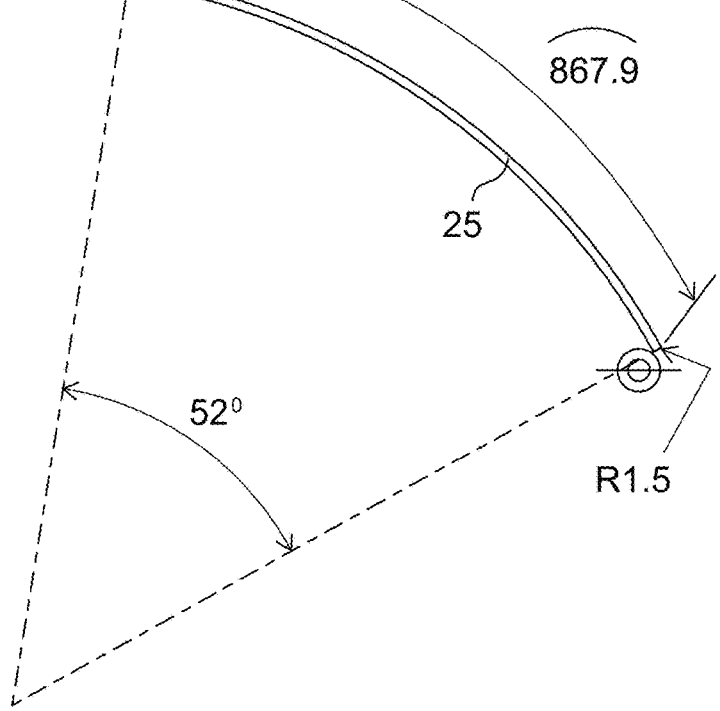
FIG. 13 indicates a second section of the rim of FIG. 11, with an arc of 52 degrees.

FIG. 11 illustrates much the same view as FIG. 6, however the rear rim members are indicated showing bosses 13 in contact therewith, and supports 27. The spacing between the bosses has been found to be beneficial. The spacing between the top two bosses of FIG. 11 is at approximately a 38 degree angle, as shown in the arc of FIG. 12. Similarly, FIG. 13 illustrates the 52 degree angle defined in an arc between the boss to the right of the 12'Oclock position and the next one around, before the 3'Oclock position. These angles are working examples of the invention but can be varied to suit different apparatus and would be understood by the person skilled in the art.

FIG. 14 is a further schematic of boss 13 on an arc, a close up from FIG. 11. FIG. 15 gives a close up of the cut-out blocks of FIG. 7, useful in the invention.

FIG. 16 a, and FIG. 16 b, illustrate boss 13 from above and then in profile showing boss support 27. In use boss 13 act against the movement in the apparatus that may be caused by the weight of the arm, or other pressures or sagging biasing the drum assembly away from where it should be positioned. The precise apparatus is aligned to a particular, precise low volume isocentre, and the patient aligned thereto for targeted tumour treatment. Any unintended movement in the drum assembly is acted against by the rim members taking the pressure and the bosses acting on the drum. There may be slippage in any direction, slight twists or distortion to any of the parts of the assembly, leading to an increase in volume/width of the isocentre applied to the patient which is undesirable.

In general terms, and as illustrated somewhat in FIGS. 6 to 11, versions of the invention which are currently under development and testing involve the use of 8 'Flange supports' which fit around the 8 bosses on the LINAC drum face, and onto which are attached 8 supporting segments which abut to the internal diameter of the gantry rims, providing a stable mounting surface against which the 'high tensile, laser cut stainless steel shims can be sandwiched. These shims are accurately cut to specific shapes and lengths so that the resulting displacement of the gantry drum that they cause, directly offsets the predictable distortions experienced at the isocentre due to the effects of gravity on the structure of the LINAC. Hence when limited offset is required, potential a small shim thickness will be used, and this will increase as the amount of offset required increases with variation in gantry angle. In this way, using combinations of variable shim thicknesses on the front and/or rear rims as required or requested by the Customer, the accuracy of the isocentre of the LINAC can be accurately controlled. The Shims are currently secured in their locations by a second supporting segment which clamps the shims against the supporting segment, using a combination of bolts and washers plus threaded and clearance penetrations in the support members.

When the shims move the drum upwards in the vertical direction, gravity ensures the return of the gantry drum to the lower position as the shim moves away from the contact point between the face of the front rim and the vertical supporting wheel on the gantry base.

However, when the shims move the drum in the Y axis, a spring loaded plunger is currently placed against the inside edge of the rear rim to cause the gantry drum to be biased in a direction keep the rear horizontal positioning wheel firmly in contact with however many shims are between the rear face of the rear rim and the horizontal wheel. When there are no shims present, the horizontal wheel is kept firmly pressed against the rear face of the rear rim. Hence the gantry drum has a biasing spring force to keep it pushed rearwards. The Biasing spring force is currently produced by a spring-loaded bolt action plunger which is secured to the topside of the gantry base, between the front and rims. The end of the bolt action plunger is capped with a Teflon based material, to minimise friction and wear on the face of the gantry rim, as it rotates with the bolt action plunger pressing against it. In later versions it is anticipated that this spring force will be generated using reciprocating cupped washers in association with linear bearings and plungers.

Because the horizontal support wheels will need to have greater clearance to the faces of the rear rim to allow for the movement of the gantry drum in the Y axis, it is anticipated that an additional clamping members, which are already designed and produced by the LINAC manufacturer, will need to be fitted to the Gantry base to secure the gantry drum to the gantry base in case of seismic activity and due to reduced lateral pressure due to the increased spacing of the horizontal support wheels.

When the modification is installed the rear horizontal support wheel will need to be exchanged from a centric bearing to an eccentric bearing. This will allow for the contact point of the rear horizontal support wheel to be moved rearwards by approximately 1.1 to make suitable clearance for the movement of the gantry drum structure in the Y axis.

Exchange of this horizontal support wheel will mean that the current isocentre position of the LINAC within the treatment room will remain unchanged and the lasers will not require any significant adjustment.

From a patient treatment aspect, there will be no difference to the existing patient setup procedures. The patient will enter the treatment room and be positioned on the treatment couch according to treatment tattoos (marked during treatment planning), and room lasers which accurately align to the LINAC isocentre. The Patient is generally planned so that the target tumour is located at the radiation isocentre of the LINAC.

Variation may be made to the forms of the inventive features, as would be understood by the person skilled in the art. The combination of features, rim members, projections/bosses and locator means, with the support wheels to press the apparatus act against distortion forces. The clever invention may be performed in many different ways using the same clear principles, as hereinbefore disclosed.

In the present specification and claims, the word "comprising" and its derivatives including "comprises" and "comprise" include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

It will be apparent to a person skilled in the art that changes may be made to the embodiments disclosed herein without departing from the spirit and scope of the invention in its various aspects.

| REFERENCE SIGNS LIST: | |
|---|---|
| 10 | Front rim members |
| 11 | Projections of 10 |
| 12 | Rear rim members |
| 13 | Projections of 12 |
| 14 | Peaks of 12 |
| 15 | Troughs of 12 |
| 16 | Drum assembly |
| 17 | Drum of 16 |
| 18 | Front face of 17 |
| 19 | Rear face of 17 |
| 20 | Support wheels |
| 21 | Arm |
| 22 | Beam collimator |
| 23 | Beam of radiation |
| 24 | Annular front rim of 18 |
| 25 | Annular rear rim of 19 |
| 26 | Support |
| 27 | Boss support |
| 28 | Blocks |
| 30 | Base portion |
| 31 | Vertical support wheels |
| 32a | Horizontal support wheel |
| 32b | Horizontal support wheel |

The invention claimed is:

1. A drum assembly for a linear accelerator comprising:
a drum having a front face including a front rim and a rear face including a rear rim,
one or more support wheels supporting the drum,
an arm extending from the front face of the drum and including a beam collimator through which a beam of radiation is emitted to form a radiation isocentre, and
one or more rear rim members associated with the rear rim, an inner surface of the one or more rear rim members being provided with one or more projections extending therefrom, the one or more projections extending between the one or more rear rim members and an inside edge of the rear rim, and the one or more rear rim members and the one or more projections adapted to reduce unintended movement of the drum assembly,
wherein the drum assembly further comprises one or more locating members associated with the rear rim, the one or more rear rim members and the one or more locating members together adapted to create or limit movement of the drum assembly in a direction that is parallel to the axis of rotation of the drum assembly such that the movement of the drum assembly offsets the equal and opposite distortion of the isocentre caused by the deflection of the arm, at particular gantry angles.

2. The drum assembly for a linear accelerator of claim 1, wherein the front face and the rear face are provided with one or more lip members at the outer edges thereof that extend at least partially about the circumference of the front face and the rear face.

3. The drum assembly for a linear accelerator of claim 1, wherein the one or more support wheels are positioned vertically relative to the drum so that the axis of rotation of the support wheels is parallel to the axis of rotation of the drum or positioned horizontally relative to the drum so that the axis of rotation of the support wheels is perpendicular to the axis of rotation of the drum.

4. The drum assembly for a linear accelerator of claim 1, wherein the one or more support wheels are a combination of vertical and horizontal support wheels wherein the vertical support wheels support the drum and facilitate rotation of the drum about a horizontal axis, and wherein the horizontal support wheels act to limit the movement of the drum across the surface of the vertical support wheels and assist in maintaining the drum in an essentially fixed position in the direction of the horizontal axis.

5. The drum assembly for a linear accelerator of claim 4, wherein the vertical support wheels are mounted to a base portion in a vertical position, while the horizontal support wheels are mounted to the base portion in a horizontal position.

6. The drum assembly for a linear accelerator of claim 1, wherein two or more rear rim members are included and each rear rim member is the same dimension as the other rear rim members, or each rear rim member is a different dimension in that each rear rim member extends for a different length about the circumference of the rear face of the rear rim.

7. The drum assembly for a linear accelerator of claim 1, wherein when the beam of radiation issues from the arm in a vertical position, and the axial movement of the drum offsets the sagging of the arm.

8. The drum assembly for a linear accelerator of claim 1, wherein the one or more rear rim members are arranged to offset the effect of gravity on the arm such that the volume of the isocentre is minimised.

9. The drum assembly for a linear accelerator of claim 1, wherein the inner surface or an upper surface of the one or more rear rim members are provided with one or more peaks or troughs such that the thickness of the one or more rear rim members varies along their length.

10. The drum assembly for a linear accelerator of claim 1, further comprising a plurality of projections spaced about the circumference of the rear rim.

11. The drum assembly for a linear accelerator of claim 1, wherein the one or more rear rim members extend outwardly beyond a rear edge of the rear rim.

12. The drum assembly for a linear accelerator of claim 1, wherein the one or more locating members are positioned to act upon the inside edge of the rear rim.

13. The drum assembly for a linear accelerator of claim 1, wherein the one or more locating members act upon the rear rim such that a force is applied to the rear rim to control or limit forward movement of the drum assembly in the direction of the horizontal axis.

14. The drum assembly for a linear accelerator of claim 1, wherein the one or more locating members include one or more locating wheels, located in abutment with, or in close proximity to, the inside edge of the rear rim and the one or more locating wheels act in concert with the one or more support wheels to support the drum.

15. The drum assembly for a linear accelerator of claim 14, wherein the one or more locating wheels are biased into position using one or more biasing members or may be associated with one or more biasing members, such that the drum is unable to overcome the bias of the one or more biasing members and unintended forward movement of the drum is reduced or eliminated.

16. The drum assembly for a linear accelerator of claim 15, wherein at least one of the one or more biasing members is located between the one or more locating wheels and the rear rim such that the drum assembly is unable to overcome the bias of the one or more biasing members, precluding unintended forward movement of the drum assembly.

17. The drum assembly for a linear accelerator of claim 1, wherein the drum assembly further comprises one or more front rim members, associated with the front rim.

18. The drum assembly for a linear accelerator of claim 17, wherein the one or more front rim members are adapted to offset sagging or twisting of the arm such that the volume of the isocentre is minimised.

19. The drum assembly for a linear accelerator of claim 17, wherein an inner surface of the one or more front rim members is provided with one or more projections extending therefrom and further wherein the one or more projections extend between an inner surface of the one or more front rim members and the front rim such that the one or more projections abut the front rim in use so as to support the one or more front rim members and fix them in position on the front face of the front rim.

20. The drum assembly for a linear accelerator of claim 1, wherein the drum assembly produces an isocentre of less than about 1 millimetres.

* * * * *